(12) United States Patent
Allen et al.

(10) Patent No.: US 6,450,015 B1
(45) Date of Patent: Sep. 17, 2002

(54) AMBIENT CONDITION SENSOR FOR A PHOTOSENSITIVE MEDIA CARTRIDGE

(75) Inventors: Loretta E. Allen, Hilton; Lee Tutt, Webster, both of NY (US)

(73) Assignee: Eastman Kodak Company, Rochester, NY (US)

( * ) Notice: Subject to any disclaimer, the term of this patent is extended or adjusted under 35 U.S.C. 154(b) by 34 days.

(21) Appl. No.: 09/732,547

(22) Filed: Dec. 8, 2000

(51) Int. Cl.⁷ .............................. G01N 5/02; H01C 7/00
(52) U.S. Cl. ..................... 73/73; 73/29.05; 338/35
(58) Field of Search ................. 73/73, 29.05; 338/35

(56) References Cited

U.S. PATENT DOCUMENTS

| | | | |
|---|---|---|---|
| 4,034,609 A | * 7/1977 | Fuller | 73/73 |
| 4,298,855 A | 11/1981 | Mills | 338/35 |
| 4,399,209 A | 8/1983 | Sanders et al. | 430/138 |
| 4,416,966 A | 11/1983 | Sanders et al. | 430/138 |
| 4,440,846 A | 4/1984 | Sanders et al. | 430/138 |
| 4,473,813 A | 9/1984 | Kinjo et al. | 338/35 |
| 4,635,027 A | 1/1987 | Miyoski et al. | 338/34 |
| 4,766,050 A | 8/1988 | Jerry | 430/138 |
| 5,028,906 A | * 7/1991 | Moriya et al. | 338/35 |
| 5,075,667 A | * 12/1991 | Nishiwaki et al. | 338/35 |
| 5,230,982 A | 7/1993 | Davis et al. | 430/138 |
| 5,348,761 A | 9/1994 | Mitter et al. | 427/101 |
| 5,608,374 A | * 3/1997 | Ikejiri | 338/35 |
| 5,783,353 A | 7/1998 | Camillus et al. | 430/138 |
| 5,879,943 A | * 3/1999 | Ando et al. | 73/73 |
| 5,884,114 A | 3/1999 | Iwasaki | 396/583 |
| 5,916,727 A | 6/1999 | Camillus et al. | 430/138 |
| 6,063,486 A | * 5/2000 | Kobayashi | 338/35 |

* cited by examiner

Primary Examiner—Hoa Van Le
(74) Attorney, Agent, or Firm—David A. Novais

(57) ABSTRACT

A photosensitive media cartridge includes an ambient condition sensor mounted in the cartridge for sensing ambient conditions in the cartridge. When the cartridge is positioned at a media transfer position on an image-forming device that permits the conveyance of media from the cartridge to the image-forming device, image development or printing on the media in the image-forming device is controlled based on the sensed ambient conditions in the cartridge. The ambient condition sensor includes a cover layer and a conductive layer, wherein a rate of response to ambient conditions of the cover layer matches rate of response to ambient conditions of the photosensitive media to be developed. As a further option, the media itself can include a conductive layer so that the media can be the sensor.

24 Claims, 14 Drawing Sheets

AMBIENT CONDITION SENSOR FOR A PHOTOSENSITIVE MEDIA CARTRIDGE

CROSS REFERENCE TO RELATED APPLICATIONS

Reference is made to commonly assigned copending applications Ser. No. 09/597,924 filed Jun. 19, 2000, entitled AN IMAGE FORMING DEVICE AND A METHOD OF PROCESSING PHOTOSENSITIVE MEDIA HAVING MICROENCAPSULATED IMAGING MATERIAL, in the names of Loretta E. Allen, Yongcai Wang, Stephen M. Reinke and Yeh-Hung Lai; and Ser. No. 09/597,928 filed Jun. 19, 2000, entitled AN IMAGING ASSEMBLY AND MEDIA CARTRIDGE HAVING COOPERATING LINKAGE ARRANGEMENTS, in the names of Loretta E. Allen, Yongcai Wang, Stephen M. Reinke and Yeh-Hung Lai; U.S. Pat. No. 6,268,094 issued Jul. 31, 2001, entitled A PHOTOSENSITIVE MEDIA CARTRIDGE HAVING AN AMBIENT CONDITION SENSOR, filed in the names of Loretta E. Allen, Yongcai Wang, Stephen M. Reinke and Lai Yeh-Hung.

FIELD OF THE INVENTION

The present invention relates to a sensor for sensing ambient conditions within a photosensitive media cartridge or at least in an environment surrounding the media or material in the cartridge. The present invention further relates to an imaging arrangement in which imaging of photosensitive material within an imaging device is controlled based on the sensed ambient conditions.

BACKGROUND OF THE INVENTION

Sensing apparatuses for sensing ambient conditions such as humidity sensors are known. There are many mechanisms by which a humidity sensor senses humidity. A few examples are conductivity, capacitance, and resistivity. Humidity sensors which utilize these mechanisms are disclosed in U.S. Pat. Nos. 4,473,813, 4,298,855, 4,635,027, and 5,348,761. These commercially available humidity sensors are typically designed to have a quick response time to changes in humidity.

Image-forming devices which process a photosensitive media or material that includes microencapsulated coloring material are known. In these imaging devices the microcapsules are exposed to a radiation based on image information. The microcapsules, whose mechanical strength can change when exposed to light, are ruptured by means of a crushing pressure, whereupon the coloring material and other substances encapsulated in the microcapsules are released and development occurs. For example, some systems use a pair of upper and lower nip rollers to apply pressure. In these systems, the photosensitive media is passed between the pair of upper and lower nip rollers which apply pressure to rupture the microcapsules and begin development. Imaging devices that employ microencapsulted photosensitive compositions are disclosed in U.S. Pat. Nos. 4,399,209, 4,416,966, 4,440,846, 4,766,050, 5,783,353, and 5,916,727.

A problem in processing photosensitive media or material having microencapsulated color-forming material is that printing and/or imaging can be adversely affected by ambient conditions. That is, ambient conditions around the photosensitive media, or in the cartridge which carries the photosensitive media, can adversely affect subsequent printing or development of the image. More specifically, ambient conditions such as humidity around the photosensitive media or in the cartridge which houses the photosensitive media, can have adverse affects on the chemicals of the coloring material, the encapsulating material, and/or the photosensitive media. Further, the degree of hardening or curing of the microcapsules and the concomitant increase in viscosity of the microcapsule varies with a change in humidity. As a result, photographic characteristics such as speed, minimum and maximum density, fogging density and full color imaging can be adversely affected.

As discussed above, commercially available humidity sensors are typically designed to have a quick response time to changes in humidity. On the other hand, photosensitive media or material tends to exhibit a slow rate of response to a change in conditions. That is, photosensitive media tends to have a slow equilibrium rate. Thus, commercially available humidity sensors do not respond at the same rate as the photosensitive media or material with the result being that these sensors do not provide a true representation of the level of relative humidity on or around the media. Therefore, if a commercially available humidity sensor having a quick response to changes in humidity were associated with photosensitive media having a slow rate of change to humidity, printing parameters for the photosensitive media would not be controlled to optimum conditions. More specifically, if a commercially available humidity sensor was used to sense humidity values in a cartridge carrying photosensitive material, when the cartridge is placed in an image-forming device, the humidity sensor would respond more rapidly to humidity conditions than the photosensitive material would. Therefore, the humidity value sensed by the humidity sensor would not be representative of the humidity value around the media. The control of printing parameters would thus be based on a humidity value which is not reflective of the level of humidity on or around the media.

SUMMARY OF THE INVENTION

The present invention provides for an ambient condition sensor, such as a humidity sensor, with a response time that is equal to or matches the response time of the photosensitive media or material; a method for manufacturing the ambient condition sensor; an image-forming device which utilizes the ambient condition sensor; and a method for processing photosensitive media which overcome the above-mentioned drawbacks.

More specifically, the present invention relates to an imaging device in which photosensitive media that contains photosensitive, rupturable microcapsules can be first exposed and then developed by applying pressure to the photosensitive media. In the image-forming device of the present invention, print image quality can be improved by sensing ambient conditions such as humidity in the image-forming device, directly from the media, or in the cartridge which carries the media, and adjusting at least one adjustable parameter based on the sensed ambient condition. As an example, in response to a sensed humidity condition, a controller or development member of the present invention can accordingly adjust the amount of pressure applied to the microcapsules.

As indicated above, in the imaging device of the present invention, the photosensitive media contains photosensitive, rupturable microcapsules that are exposed and then developed by the application of pressure using a stylus or pinch rollers to rupture unexposed microcapsules. Thereafter, the developed print may be fixed with heat supplied by a heater in the imaging device. In the invention, the level of relative humidity can be sensed inside and/or outside of the image-forming device, in the media cartridge or directly on the photosensitive media, and then at least one of the parameters of light exposure, developing pressure, printing speed or fixing temperature can be adjusted automatically on the basis of the relative humidity level to provide an improved image. As an example, by adjusting the printing speed for a printer, the so-called "dark time" which is the time between exposure and development will be changed. The dark time affects the hardness of microcapsules and therefore their crushability. Also, within the context of the present invention, the concept of sensing the level of relative humidity on the photosensitive media refers to sensing the moisture content on or around the photosensitive media or material.

The present invention accordingly relates to an ambient condition sensor for sensing ambient conditions in a cartridge which holds photosensitive material. The ambient condition sensor comprises a top layer, a humidity responsive layer, a conductive layer and a base support layer. In the invention, a rate of response to ambient conditions of at least one of the top layer, the humidity responsive layer, and the base support layer matches a rate of response to ambient conditions of photosensitive material in the cartridge.

The present invention further relates to a photosensitive material which comprises a transparent support layer, an imaging composition layer, a conductive layer and a base layer. The photosensitive material is positioned in a cartridge which holds photosensitive material to be developed and is adapted to sense ambient conditions around the photosensitive material in the cartridge.

The present invention further relates to a photosensitive media cartridge which comprises a housing adapted to hold a stack of photosensitive media; and an ambient condition sensor positioned within the housing for sensing ambient conditions around photosensitive media in the housing and providing an ambient condition signal indicative thereof. A development of the photosensitive media is based on the sensed ambient conditions. The ambient condition sensor comprises a transparent top layer, a humidity responsive layer, a conductive layer and a base support layer. A rate of response to ambient conditions of at least one of the transparent top layer, the humidity responsive layer, and the base support layer matches a rate of response to ambient conditions of the photosensitive media in the housing.

The present invention further relates to a photosensitive media cartridge which comprises a housing adapted to hold a stack of photosensitive media, such that at least one of the photosensitive media in the stack of photosensitive media comprises a transparent support layer, an imaging composition layer, a conductive layer and a base layer. At least one photosensitive media having the conductive layer is adapted to sense ambient conditions around the photosensitive media in said housing.

The present invention further relates to an image-forming arrangement which comprises an image-forming device for forming a latent image on a photosensitive media; and a media cartridge for holding a stack of photosensitive media therein. The media cartridge is adapted to be inserted into the image-forming device to permit a conveyance of the photosensitive media to the image-forming device. The media cartridge comprises an ambient condition sensor for sensing ambient conditions around media in the cartridge, such that a development of the photosensitive media in the image-forming device is based on the sensed ambient conditions. The ambient condition sensor comprises a transparent top layer, a humidity responsive layer, a conductive layer and a base support layer, wherein a rate of response to ambient conditions of at least one of the transparent top layer, the humidity responsive layer, and the base support layer matches a rate of response to ambient conditions of the photosensitive media in the media cartridge.

The present invention further relates to an image-forming arrangement which comprises an image-forming device for forming a latent image on a photosensitive media; and a media cartridge adapted to hold a stack of photosensitive media, wherein at least one of the photosensitive media in the stack of photosensitive media comprises a transparent support layer, an imaging composition layer, a conductive layer and a base layer. The at least one photosensitive media having the conductive layer is adapted to sense ambient conditions around the photosensitive media in the housing and a development of the photosensitive media in the image-forming device is based on the sensed ambient conditions.

The present invention further relates to a photosensitive media cartridge which comprises a housing adapted to hold a stack of photosensitive media, such that all of the media in the stack of photosensitive media comprises a transparent support layer, an imaging composition layer, a conductive layer and a base layer. The photosensitive media having the conductive layer is adapted to sense ambient conditions around the photosensitive media in said housing. arrangement which comprises an image-forming device for forming a latent image on a photosensitive media; and a media cartridge adapted to hold a stack of photosensitive media, wherein all of the media in the stack of photosensitive media comprises a transparent support layer, an imaging composition layer, a conductive layer and a base layer. The photosensitive media having the conductive layer is adapted to sense ambient conditions around the photosensitive media in the housing and a development of the photosensitive media in the image-forming device is based on the sensed ambient conditions.

The present invention further relates to a method of producing an ambient condition sensor for photosensitive material to be developed. The method comprises providing at least one cover layer on a conductive layer; and placing the conductive layer having at least one cover layer thereon in a cartridge which is adapted to hold photosensitive material to be developed therein, such that a rate of response to ambient conditions of at least the cover layer matches a rate of response to ambient conditions of the photosensitive material in the cartridge.

The present invention further relates to a method of controlling image development which comprises providing an ambient condition sensor in a cartridge which holds photosensitive media therein, with the ambient condition sensor sensing ambient conditions around photosensitive media in the cartridge, the ambient condition sensor comprising at least a cover layer and a conductive layer, and a rate of response to ambient conditions of at least the cover layer matches a rate of response to ambient conditions of the photosensitive media in the media cartridge; inserting the cartridge to an insertion position in an imaging device which permits a passage of photosensitive media from the cartridge to the imaging device; sensing ambient conditions around the photosensitive media by way of the ambient condition sensor; and controlling a development of images on the photosensitive media based on the sensed ambient conditions.

The present invention further relates to an ambient condition sensor for a photosensitive material imaging arrangement which comprises a cover layer and a conductive layer, wherein a rate of response to ambient conditions of the cover layer matches a rate of response to ambient conditions of a photosensitive material to be developed.

DETAILED DESCRIPTION OF THE INVENTION

Figure 1:
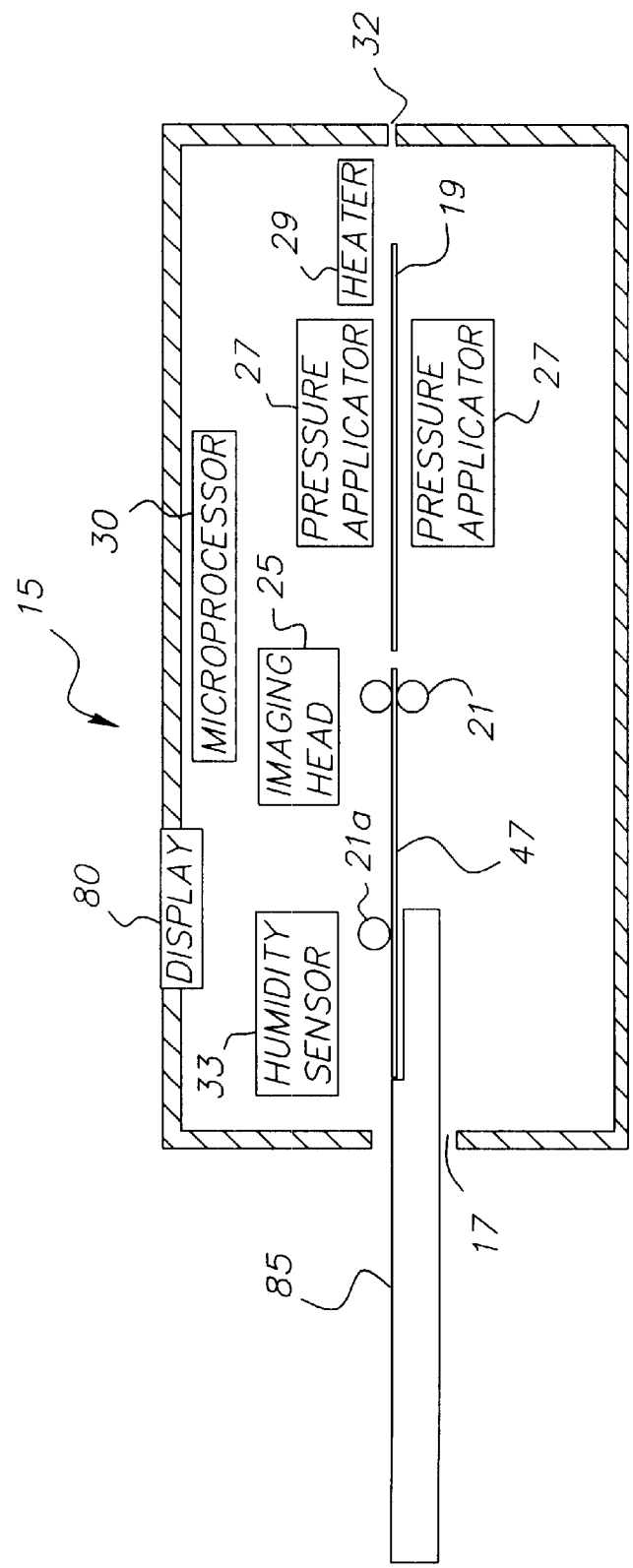
FIG. 1 schematically illustrates one example of an image-forming arrangement in accordance with the present invention.

Referring now to the drawings, wherein like reference numerals represent identical or corresponding parts throughout the several views, FIG. 1 is a schematic view of an image-forming device 15 of the present invention. Image-forming device 15 could be, for example, a printer that includes an opening 17 which is adapted to receive a cartridge 85 containing photosensitive media 47. As described in U.S. Pat. No. 5,884,114, the cartridge could be a light-tight cartridge in which photosensitive sheets, media or material are piled one on top of each other. When inserted into image-forming device 15, a feed mechanism which includes, for example, a feed roller 21a in image-forming device 15, working in combination with a mechanism in the cartridge, cooperate with each other to pull one sheet at a time from the cartridge into image-forming device 15 in a known manner. Once inside image-forming device 15, photosensitive media 47 travels along media path 19, and is transported by, for example, drive rollers 21 connected to, for example, a driving mechanism such as a motor. The photosensitive media will pass by an imaging head 25 which could include a plurality of light emitting elements that are effective to expose a latent image on the photosensitive media based on image information. After the latent image is formed, the photosensitive media is conveyed past a development member such as a pressure applicator or pressure assembly 27, where an image such as a color image is formed based on the image information by applying pressure to microcapsules having imaging material encapsulated therein to crush the microcapsules. Within the context of the present invention, the imaging material comprises a coloring material (which is used to form images) or material for black and white media. After the formation of the image, the photosensitive media is conveyed past a heater 29 for fixing the image on the media. In a through-feed unit, the photosensitive media could thereafter be withdrawn through an exit 32. As a further option, image-forming device 15 can be a return unit in which the photosensitive media is conveyed or returned back to opening 17.

Figure 2:
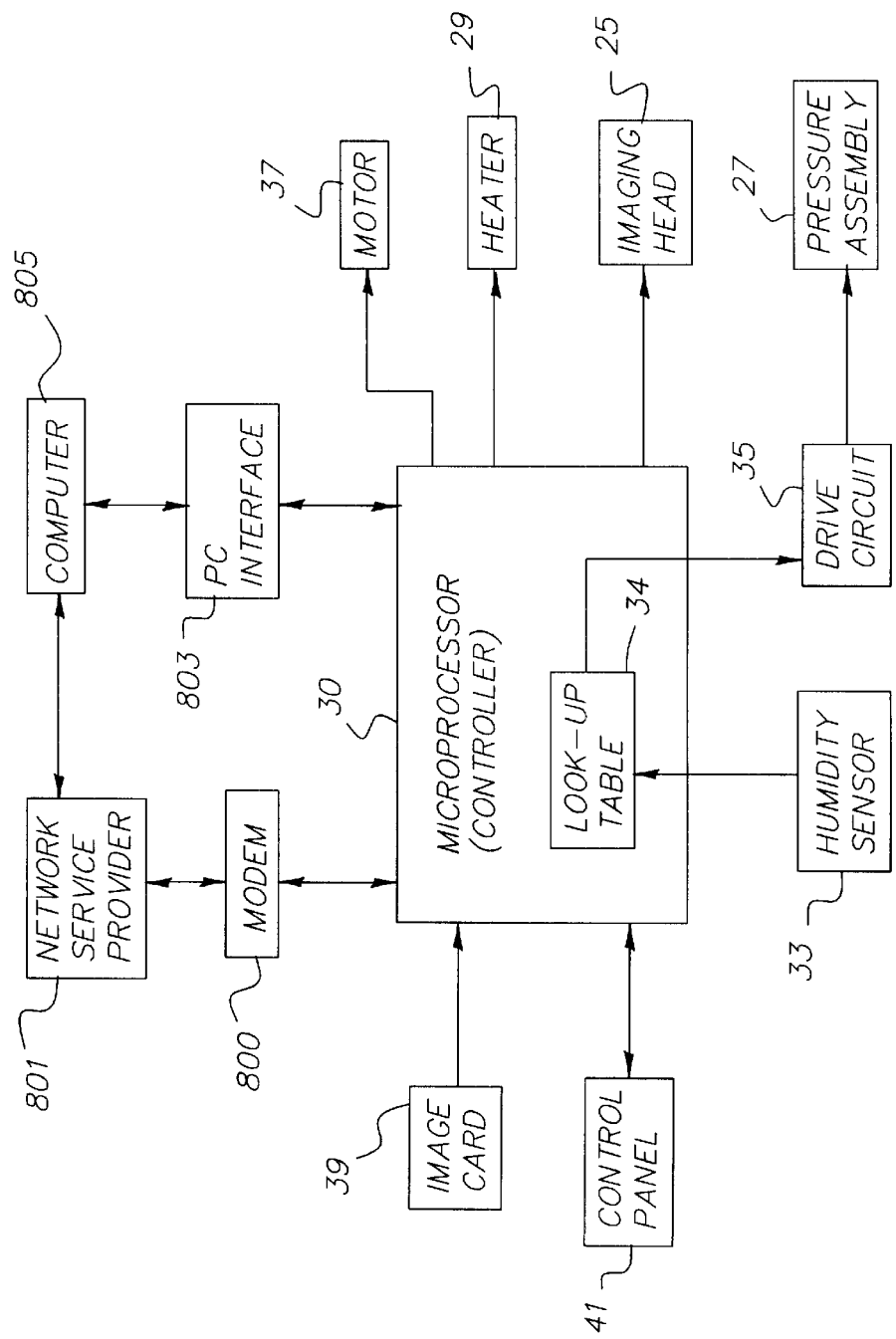
FIG. 2 schematically illustrates a microprocessor for controlling the operation of the image-forming arrangement of FIG. 1.

In a feature of the present invention, image-forming device 15 includes a microprocessor or controller 30, illustrated in detail in FIG. 2. Controller 30 controls several printing parameters with respect to the development of the image on the photosensitive media. For example, controller 30 can control parameters such as light exposure, pressure application, fixing temperature, printer motor speed, etc.

With reference to FIG. 2, a first feature of image-forming device 15 and controller 30 of the present invention is the control of printing conditions based on sensed ambient conditions. More specifically, controller 30 is adapted to be responsive to ambient conditions to provide a pressure increasing or pressure decreasing signal to pressure assembly 27 to control the amount of pressure or crushing force applied by pressure assembly 27.

In one example of the invention as illustrated in FIG. 2, controller 30 is operationally associated with an ambient condition sensor which senses ambient conditions within image-forming device 15. As shown in FIG. 2, the ambient condition sensor can be a humidity sensor 33 which senses humidity conditions within image-forming device 15. As will be explained in detail later, the invention is not limited to sensing the humidity within image-forming device 15. It is noted that the humidity can be sensed outside of image-forming device 15. Within the context of the present invention, the humidity is sensed within a photosensitive media cartridge and/or directly from or around the photosensitive media itself.

Once the humidity is sensed by humidity sensor 33, a signal indicative thereof is sent to a look-up table 34. Look-up table 34 can include a plurality of reference humidity values which are compared to the sensed humidity value. Within the context of the present invention, the term reference humidity value refers to a humidity level or more preferably, a response curve (printing pressure vs. humidity). As a further option, rather than using a look-up table, an equation or a direct circuit can be utilized. Once this comparison is made, controller 30 can drive a drive circuit 35 for controlling the pressure application by pressure assembly 27. As an example, it is beneficial to apply a larger amount of pressure when a sensed humidity is high (for example, higher than a reference humidity value of 30%) and to reduce the pressure applied to the photosensitive material when the sensed humidity is low (for example, lower than a reference humidity value of 30%). Of course, it is noted that the present invention is not limited to the above-reference humidity value. It is noted that the reference humidity value can be any value which is set based on a desired result. As an example, a reference humidity value which provides consistent sensitometric properties can be used.

As a further example, it is beneficial to reduce the pressure applied to the photosensitive material, or increase the level of light exposure, or to reduce the printing speed when the sensed humidity is low. These changes can be done according to precalibrated information stored in the printer or stored on the cartridge through a barcode. Under certain conditions, it is desirable to change several parameters simultaneously according to the humidity information to optimize the printing conditions.

The precalibrated information for a given type of media can be obtained by testing the sensitometric characteristics of the media as a function of, for example, printing pressure or light exposure level. The details of response of printing pressure to humidity depend on the media. But it is in general theorized that the mechanical properties of a microcapsule containing layer changes with humidity which in turn changes the response of the microcapsule containing layer to printing pressure. For example, if the microcapsule containing layer is rigid at lower humidity (e.g. 30% RH) the microcapsules are more easily ruptured. If the microcapsule layer becomes more flexible at high humidity (e.g. 80%RH) the microcapsules are more difficult to rupture. This may change the amount of coloring materials released by the microcapsules during the printing process. Thus, the reference humidity depends on the type of media and level of light exposure.

Therefore, if the sensed humidity is higher than the reference humidity value, the drive circuit will provide a signal to pressure assembly 27 to increase the amount of pressure applied to the photosensitive media, and if the humidity value is lower, the drive circuit will provide a signal to pressure assembly 27 to reduce the amount of pressure applied to the photosensitive media.

As also indicated above, controller 30 is adapted to control features of imaging head 25, heater 29, as well as a motor 37 for driving rollers 21 and conveying media 47 through image-forming device 15 to control printing speed. As a further option, these features could also be controlled based on the sensed humidity value. Further features of image-forming device 15 and controller 30 include the provision of a control panel 41 to enable user control of image-forming device 15, an image card 39 which can include image information with respect to the image which is to be developed and printed, and a display 80 (FIG. 1) for displaying information, such as image information or the sensed humidity value.

As a further option, images which are to be printed by image-forming device 15 can be transferred or uploaded to image-forming device 15 by way of the Internet or a computer. For example, as shown in FIG. 2, image-forming device 15 or controller 30 can include a modem 800 for communication to a network service provider 801 such as the Internet. This permits a transfer of images to image-forming device 15 from the Internet for subsequent printing. As a further example, image-forming device 15 or controller 30 can include a PC interface 803 in communication with a computer 805 such as a personal computer. This permits the transfer of images stored in computer 805 to image-forming device 15 for subsequent printing. As a further option, computer 805 can be communicated to Network service provider 801 to download images from the Internet to image-forming device 15 via computer 805.

Figure 3A:
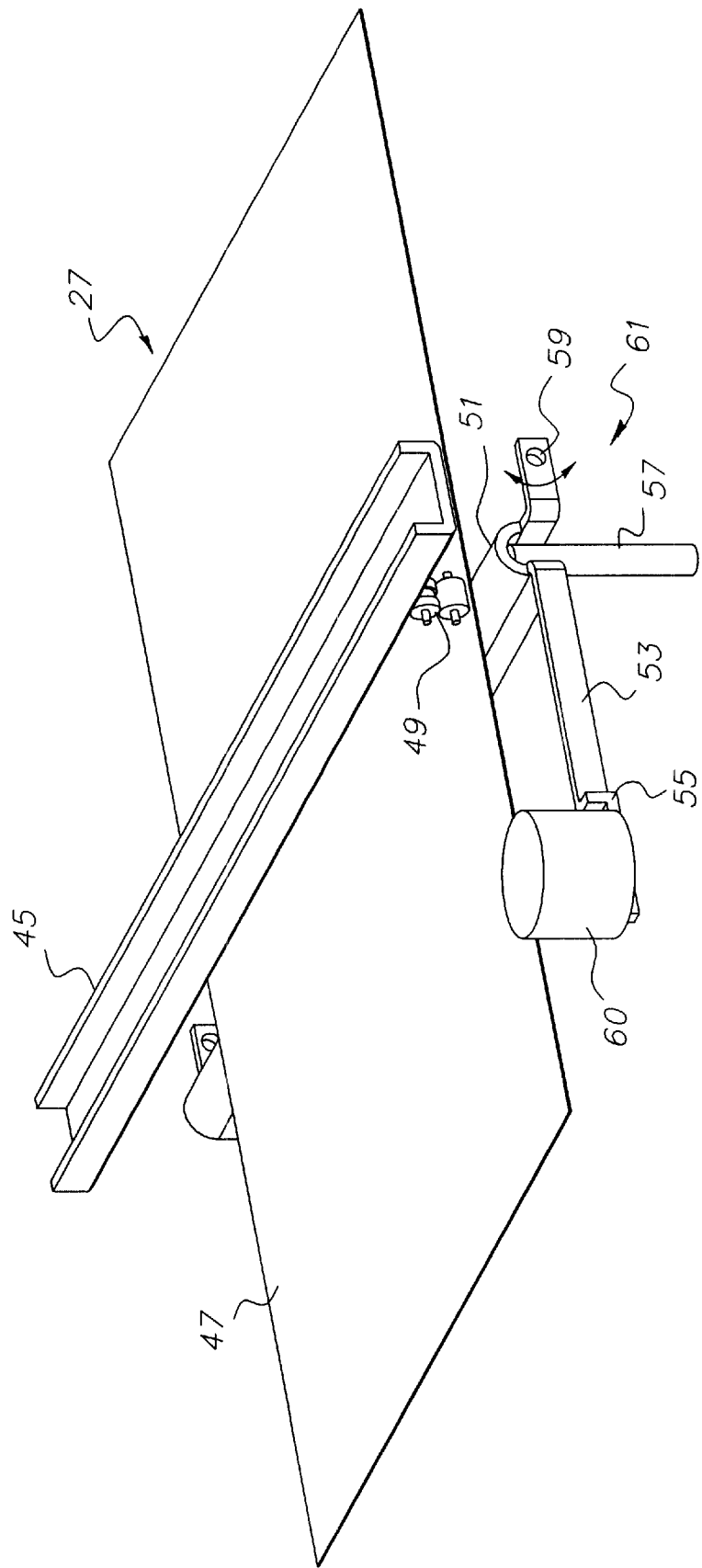
FIG. 3(a) illustrates a first embodiment of a pressure applying assembly of the image-forming arrangement of the present invention.
Figure 3B:
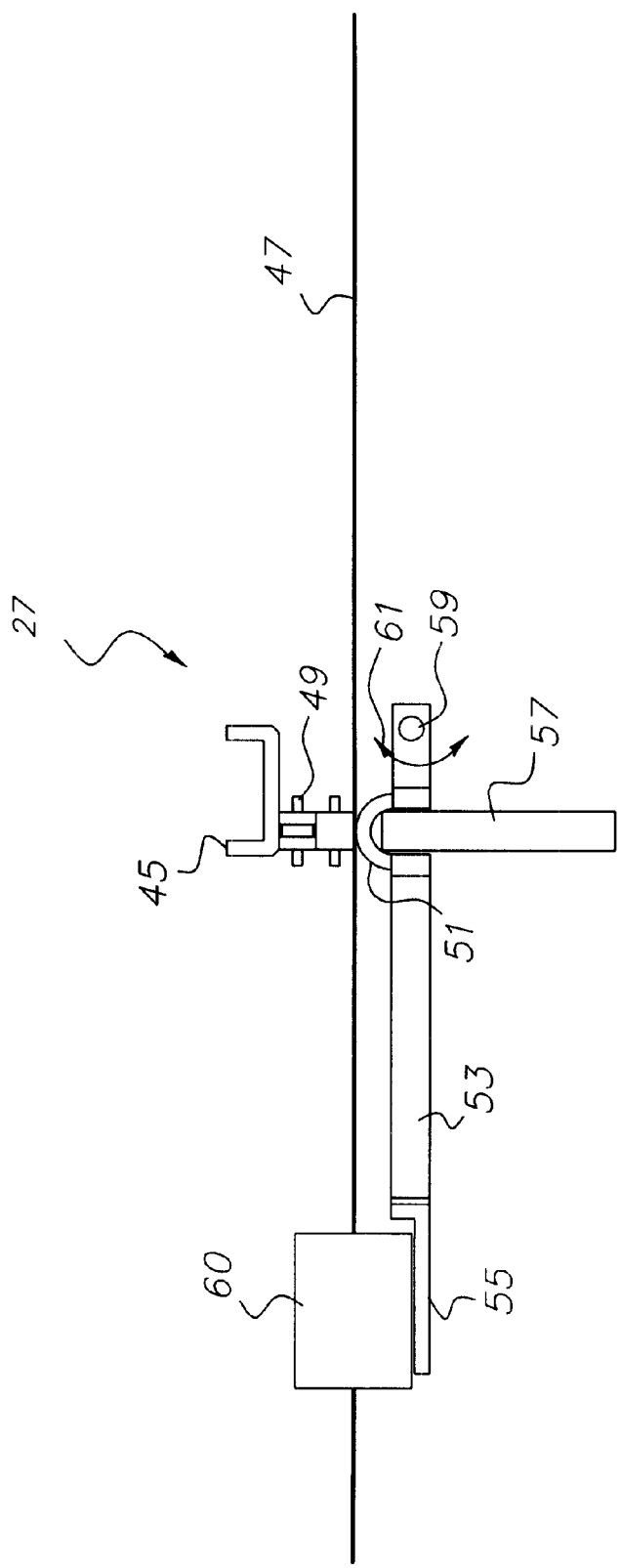
FIG. 3(b) is a side view of the pressure applying assembly of FIG. 3(a).
Figure 3C:
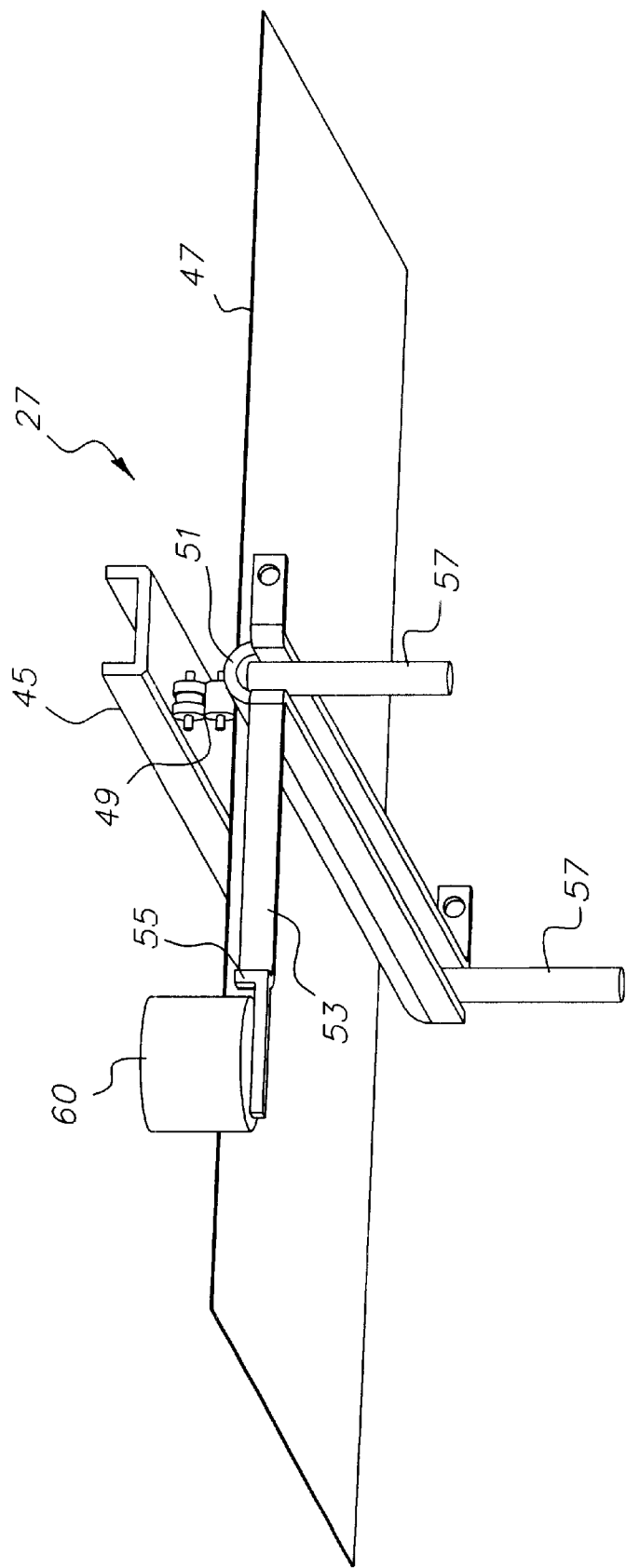
FIG. 3(c) is a further view of the pressure applying assembly of FIG. 3(a)

FIGS. 3(a), 3(b) and 3(c) illustrate different views of an embodiment of pressure assembly 27 in accordance with the present invention. Pressure assembly 27 can comprise a crushing roller and beam arrangement which provides a point contact on photosensitive media 47. More specifically, pressure assembly 27 includes a slide 45 which extends along a width-wise direction of a photosensitive media 47. Moveably mounted on slide 45 is a crushing roller arrangement 49 which is adapted to move along the length of slide 45, i.e., across the width of photosensitive media 47. Crushing roller arrangement 49 is adapted to contact one side of photosensitive media 47. A beam 51 is positioned so as to contact the opposite side of photosensitive media 47 and is located opposite crushing roller 49. Beam 51 and crushing roller arrangement 49 when in contact with photosensitive media 47 on opposite sides provide a point contact on photosensitive media 47. Crushing roller arrangement 49 is adapted to move along a width-wise direction of photosensitive material 47 so as to crush microcapsules, release coloring material, and process image information such as image information provided by image card 39.

Extending from beam 51 is an arm 53 having an extension or seat portion 55. Also provided on beam 51 are compression springs 57 which urge beam 51 into contact with a lower side of photosensitive media 47. It is further noted that beam 51 and arm 53 are pivotally mounted at a pivot point 59 so as to be movable or rotatable about pivot point 59 as illustrated by arrow 61. Thus, compression spring 57 urges beam 51 and arm 53 in a clockwise direction about pivot point 59, so as to urge beam 51 into contact with the lower surface of media 47. In a further feature of pressure assembly 27 as illustrated in FIGS. 3(a)–3(c), an electromagnet 60 is positioned adjacent to extension 55.

Thus, compression spring 57 urges beam 51 in a clockwise direction so as to place beam 51 in a pressure applying position. Electromagnet 60 mounted to a printer frame (not shown) applies an initial attraction force to extension 55 and arm 53 so as to help maintain beam 51 in the pressure applying position. As illustrated in FIG. 2, pressure assembly 27 receives a signal from controller 30. In the embodiment of FIGS. 3(a)–3(c), electromagnet 60 is operationally connected to controller 30 via drive circuit 35.

An operation of pressure assembly 27 will now be described. With reference to FIGS. 1, 2 and 3(a)–3(c), in one embodiment of the invention, humidity within the housing of image-forming device 15 is sensed by humidity sensor 33. This provides a signal to look-up table 34 within controller 30. If the sensed humidity is above a humidity reference value or response curve, a pressure-increasing signal will be applied to drive circuit 35 so as to increase the pressure applied by pressure assembly 27. More specifically, in response to a pressure increasing signal, controller 30 will interact with electromagnet 60 to increase the attraction force on extension 55 and in turn on arm 53, and therefore increase the initial attraction force to further pivot arm 53 and beam 51 in the clockwise direction towards photosensitive media 47. This increases the pressure applied by beam 51 on photosensitive media 47, and increases the crushing force applied to the microcapsules via beam 51 and crushing roller 49. If the humidity sensed by humidity sensor 33 is below a reference humidity value, controller 30 will provide a signal to drive circuit 35 to decrease the pressure applied by pressure assembly 27. In this scenario, controller 30 will interact with electromagnet 60 to reduce the attraction force back to the initial attraction force. Thus, when electromagnet 60 receives a signal from controller 30 indicating that the sensed humidity is lower than a reference humidity, a pressure decreasing signal is provided by controller 30 to electromagnet 60. The signal causes electromagnet 60 to reduce the attraction force against arm 53 back to the initial attraction force, and thus return beam 51 and arm 53 to its initial pressure applying position.

It is noted that the structure of the pressure assembly 27 is not limited to the embodiment shown in FIGS. 3(*a*)–3(*c*). As examples, the pressure assembly can take to form of a full length clamping spring responsive to a magnetic force; or a pulley and extension spring arrangement which is actuated by a motor (see, for example, copending application Ser. No. 09/597,924).

Figure 4A:
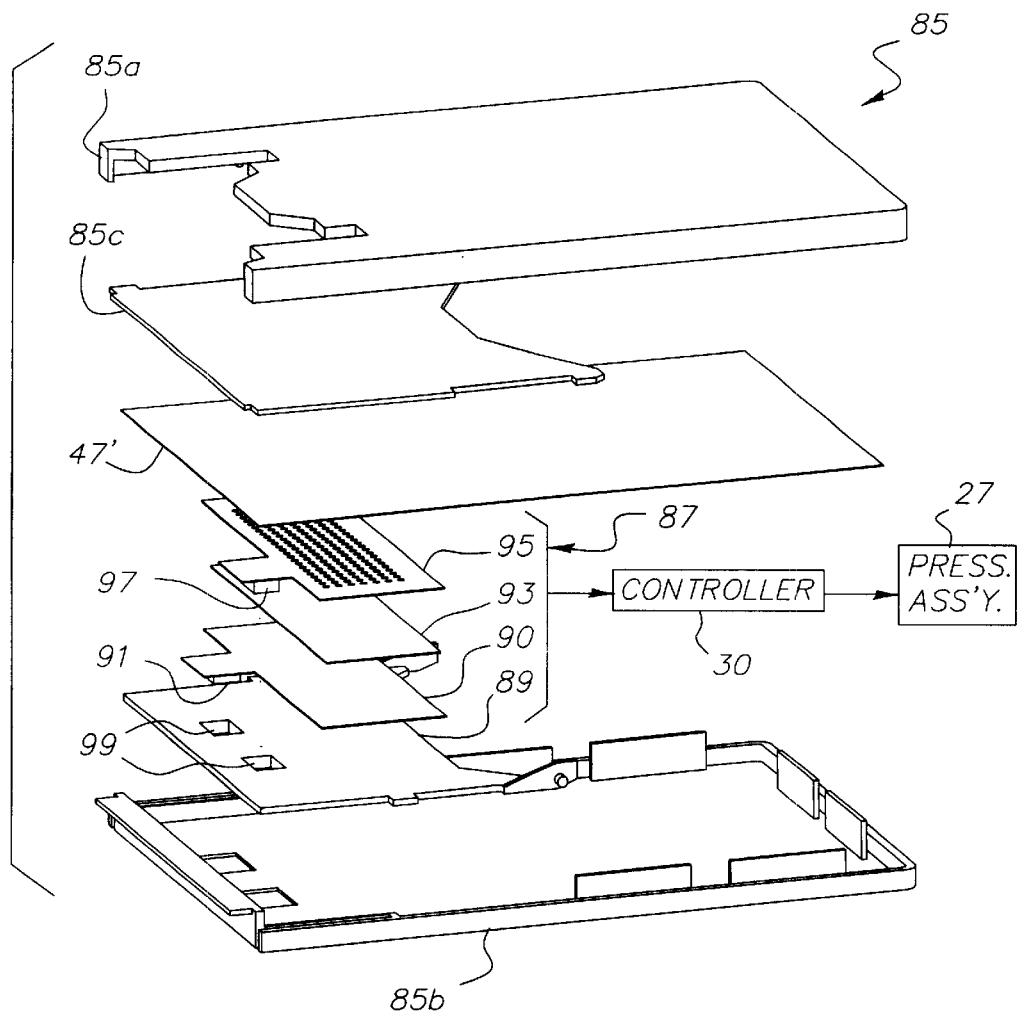
FIG. 4(a) shows a device for sensing ambient conditions in a photosensitive media cartridge in accordance with one feature of the invention.
Figure 4B:
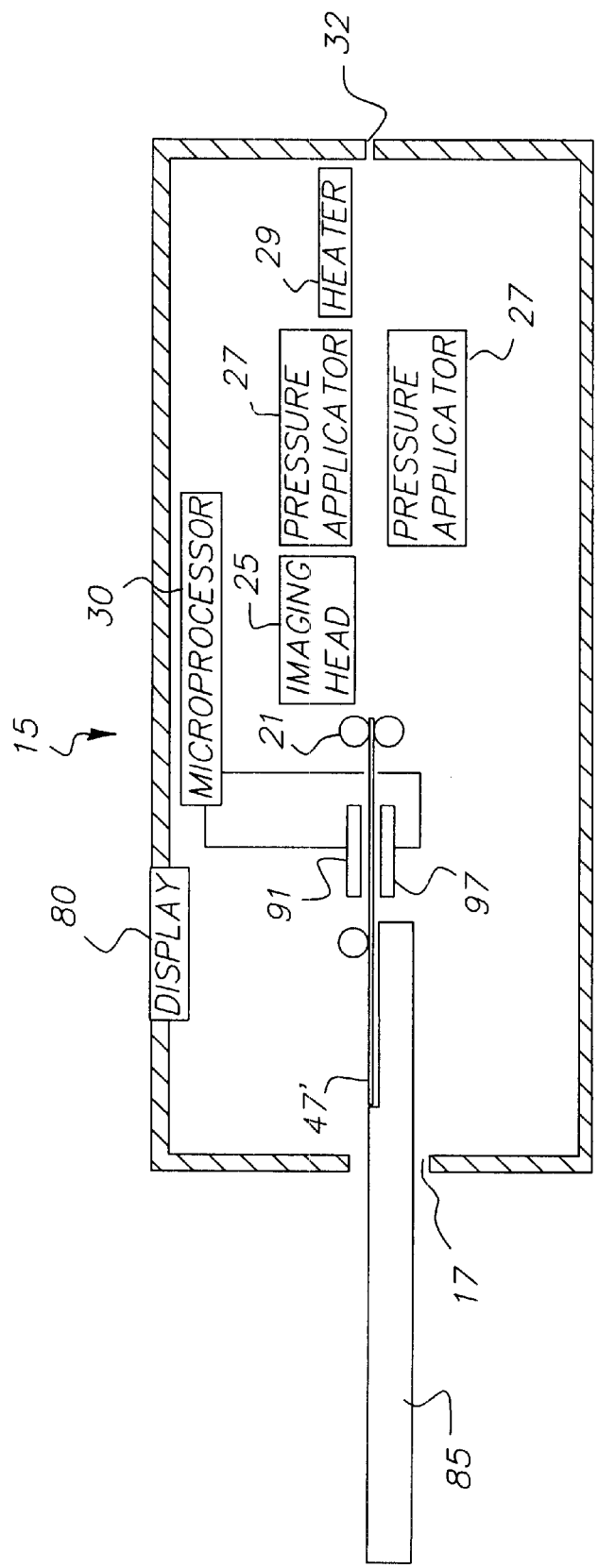
FIG. 4(b) shows a device for sensing ambient conditions in an image forming device in accordance with the present invention.
Figure 4C:
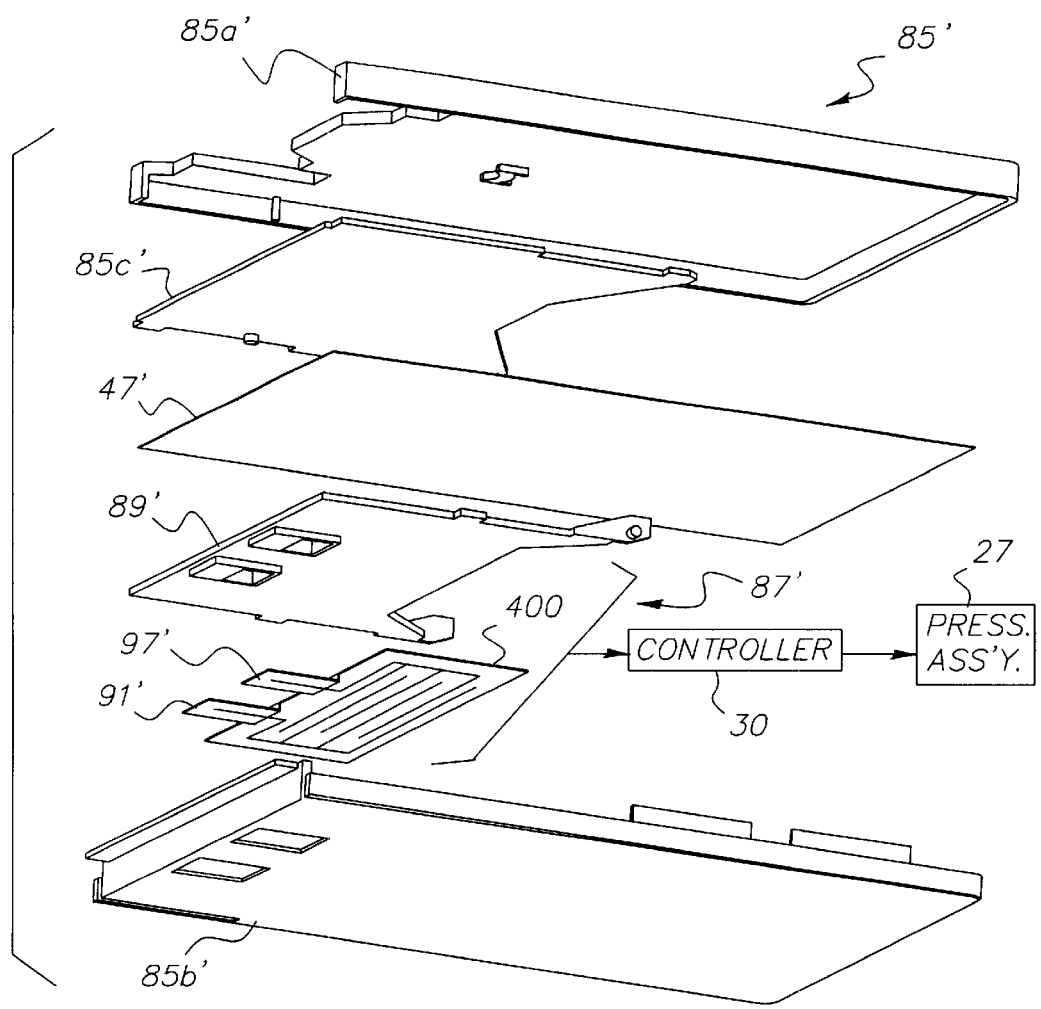
FIG. 4(c) shows another device for sensing ambient conditions in a photosensitive media cartridge in accordance with a further feature of the invention.

The invention has thus for been described with respect to measuring ambient conditions such as humidity within the housing of image-forming device 15. As previously indicated, the invention is not limited to such an arrangement. For example, the humidity within a cartridge which holds photosensitive media that is to be fed into image-forming device 15 can be sensed. FIGS. 4(*a*) and 4(*c*) illustrate embodiments for sensing humidity within a cartridge.

More specifically, FIG. 4(*a*) is an exploded view of a cartridge 85 that holds photosensitive media 47'. Media 47' could be of the type having microcapsules with coloring material. As shown in FIG. 4(*a*), media cartridge 85 defines a housing having top and bottom sections 85*a*, 85*b* which can snap together to house media 47' therein, one on top of the other. Cartridge 85 further includes a light-lock door 85*c* and a spring plate 89. Cartridge 85 and more specifically, one of the sections 85*a*, 85*b* of cartridge 85 includes a humidity sensor 87 which comprises a first contact plate 90 having a first electrode 91 and a second contact plate 95 having a second electrode 97. Sandwiched between first and second contact plates 90 and 95 is a sampling member or dielectric layer 93. Sampling member 93 could be a material which is susceptible or responsive to humidity conditions within cartridge 85. An example of this could be a salt solution impregnated fabric or various hydrophilic polymers.

Therefore, in the arrangement of FIG. 4(*a*), electrodes 97 and 91 provide for a capacitor and the measured humidity is a function of capacitance. Electrodes 97 and 91 protrude through cutouts 99 in spring plate 89 and corresponding cutouts in section 85*b* to make physical contact between sensor 87 located within cartridge 85 and controller 30 located within image-forming device 15. Based on the signal from humidity sensor 87, controller 30 controls the application of pressure by way of pressure assembly 27 in the manner described with respect to FIGS. 3(*a*)–3(*c*). Humidity sensor 87 as illustrated in FIG. 4(*a*) can replace humidity sensor 33 in the housing of image-forming device 15 or be used in addition to sensor 33. As previously described, a higher humidity would provide a signal to increase the pressure applied by pressure assembly 27, while a lower humidity would provide a signal to controller 30 to control the pressure assembly to lower the crushing pressure. Thus, an image-forming arrangement or assembly would be comprised of at least the cartridge and the image-forming device.

FIG. 4(*b*) illustrates another method for measuring humidity as a function of capacitance could be done within the housing of image-forming device 15. In this example, electrodes 91 and 97 are mounted at a predetermined distance apart from each other and are located in the media path. As media 47' travels through image-forming device 15 along the media path, it momentarily pauses when a sufficient area of media is located between the contact plates. Media 47' would now be used as the sampling member, and a measurement for capacitance is made.

FIG. 4(*c*) illustrates another embodiment for sensing humidity within a cartridge. More specifically, FIG. 4(*c*) is an exploded view of a cartridge 85' that holds photosensitive media 47'. Media 47' could be of the type having microcapsules with coloring material. As shown in FIG. 4(*c*), media cartridge 85' define a housing having top and bottom sections 85*a'*, 85*b'* which can snap together to house media 47' therein, one on top of the other. Cartridge 85' further includes a light lock door 85*c'* and a spring plate 89'. Cartridge 85' and more specifically, one of the sections 85*a'*, 85*b'* of cartridge 85' includes a humidity sensor 87' which comprises a substrate 400 with interdigitated conductive terminals on the substrate overcoated with a humidity responsive material such as a hydrophilic polymer. An example of this device comprises an ESTAR™ substrate onto which a 1000–2000Å thick layer of nickel is deposited. The interdigitated terminal pattern can be formed by laser ablation. The humidity responsive material can be a layer comprising gelatin and an antistat agent such as a quarternary amine compound. The humidity responsive material is evenly coated onto to the conductive terminals leaving a portion of the terminals exposed for electrical contacts. Humidity effects the electrical properties of the polymer and the relative humidity can be obtained directly from the equivalent resistance or conductance of the sensor. Electrodes 91' and 97' protrude through cut-outs in bottom section 85*b'* of cartridge 85' to make physical contact between sensor 87' located within cartridge 85' and controller 30 located within image-forming device 15.

Referring now to FIGS. 5(*a*) and 5(*b*), an embodiment of a humidity sensor 500 in accordance with the present invention is shown. More specifically, sensor 500 in accordance with the present invention is designed to have a response time that is equal to or matches the response time of photosensitive media. Sensor 500 basically includes a humidity sensitive member such as a humidity responsive layer 501. As an example, humidity responsive layer 501 is preferably a material comprising approximately 762 mg/m$^2$ gelatin and approximately 76.2 mg/m$^2$ of a quarternary amine compound called Cyastat SP Antistatic. Of course, the example given above is a non-limiting example, and it is recognized that other types of humidity responsive materials can be utilized. It is further recognized that the above noted proportion of the materials can be varied based on design considerations. Humidity effects the electrical properties of humidity responsive layer 501 and the relative humidity can be obtained directly from the equivalent resistance or conductance of the sensor. Humidity sensor 500 further includes a top support 503 and a base support 505. Sandwiched between base support 505 and humidity responsive layer 501 is a conductive layer 507 which includes interdigited fingers having first and second electrical contacts 509*a*, 509*b*. A feature of sensor 500 is that a layer, for example, at least one of humidity responsive layer 501, top support 503 or base support 505 is made of a material having properties which are similar or match the properties of photosensitive material 47' in media cartridge 85 or 85'. More specifically, at least one of humidity responsive layer 501, top support 503 and base support 505 has a rate of response to ambient conditions, such as relative humidity, in and around the photosensitive media, which matches the rate of response to ambient conditions of the photosensitive material. For example at least one of humidity responsive layer 501, top support 503 and base support 505 is a barrier to the diffusion of water at a rate that matches the rate of water diffusion of media in the cartridge. With this arrangement, sensor 500 would essentially be pre-calibrated to the photosensitive media in the cartridge. Therefore, when the cartridge is inserted into image-forming device 15, the ambient conditions as sensed by ambient condition sensor 500 would essentially be reflective of the ambient conditions of the photosensitive material. For example, if the photosensitive material has a slow rate of response when a cartridge is inserted into the image-forming device, the rate of response of sensor 500 would match the rate of response of the photosensitive material so as to provide for a true measure of the level of humidity on the photosensitive media. This signal is provided to controller 30 as described with respect to, for example FIGS. 4(a), 4(c), via contacts 509a, 509b. More specifically, contacts 509a, 509b protrude through cutouts in cartridge 85 or 85' to make physical contact between sensor 500 located within the cartridge and controller 30 located within image-forming device 15 to control development of the photosensitive material. Thus, an image-forming arrangement would be comprised of at least a cartridge which holds sensor 500 and image-forming device 15.

Figure 5A:
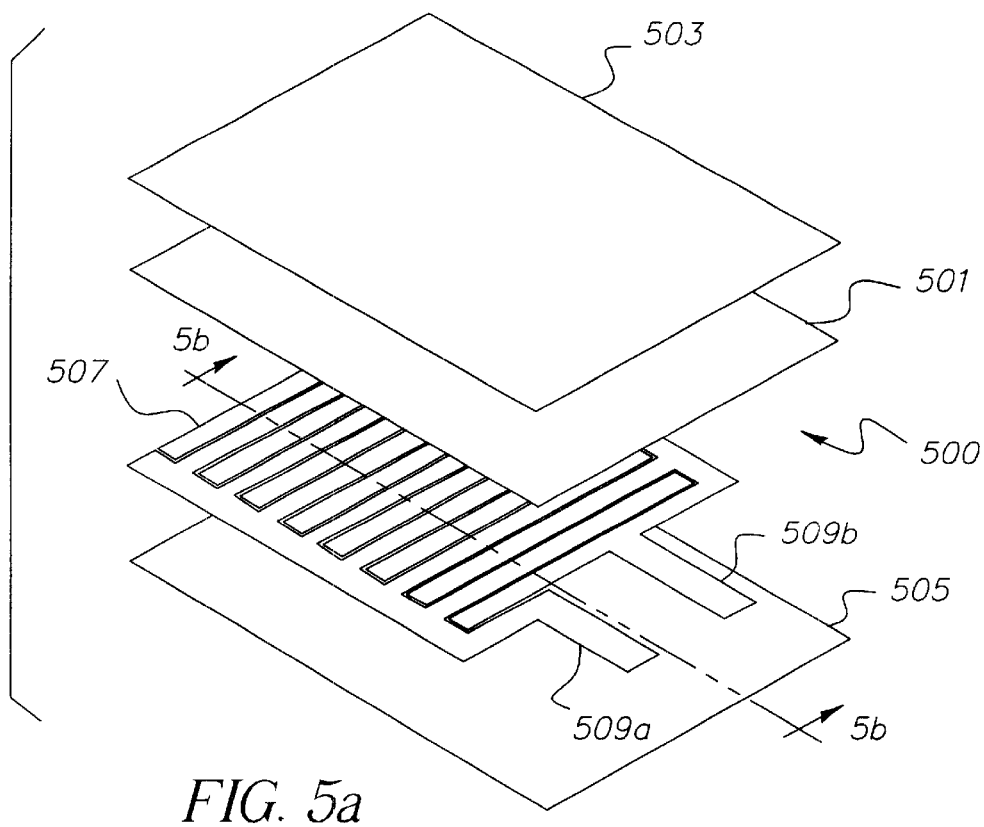
FIG. 5(a) shows an ambient condition sensor in accordance with the present invention.
Figure 5B:
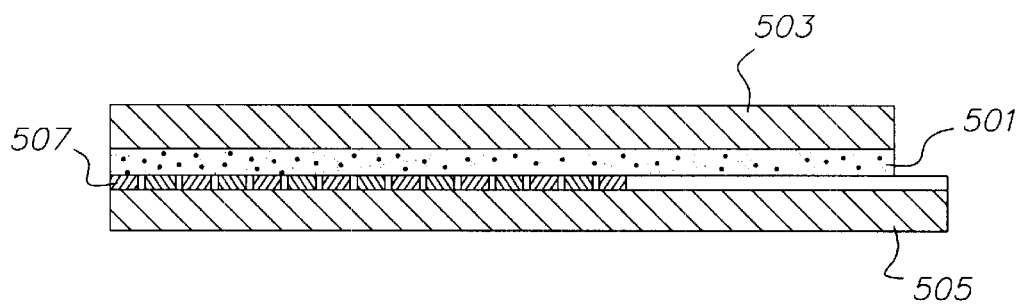
FIG. 5(b) is a cross sectional view of FIG. 5(a) taken along line 5b—5b.

As illustrated in FIG. 5(b), in a preferred embodiment of ambient condition sensor 500, top support 503 and humidity responsive layer 501 have a length which does not extend over electrical contacts 509a, 509b. On the other hand, the length of base support 505 matches the length of conductive layer 507 including electrical contacts 509a, 509b. This permits a portion of electrical contacts 509a, 509b to be exposed on one side.

It is noted that the use of ambient condition sensor 500 as illustrated in FIGS. 5(a), 5(b) is not limited to the imaging arrangements described in the present specification. More specifically, ambient condition sensor 500 as illustrated in FIGS. 5(a), 5(b) can be utilized in any type of imaging arrangement in which development of photosensitive media in the imaging arrangement is based on ambient conditions such as humidity on the photosensitive media located in a cartridge.

Figure 6A:
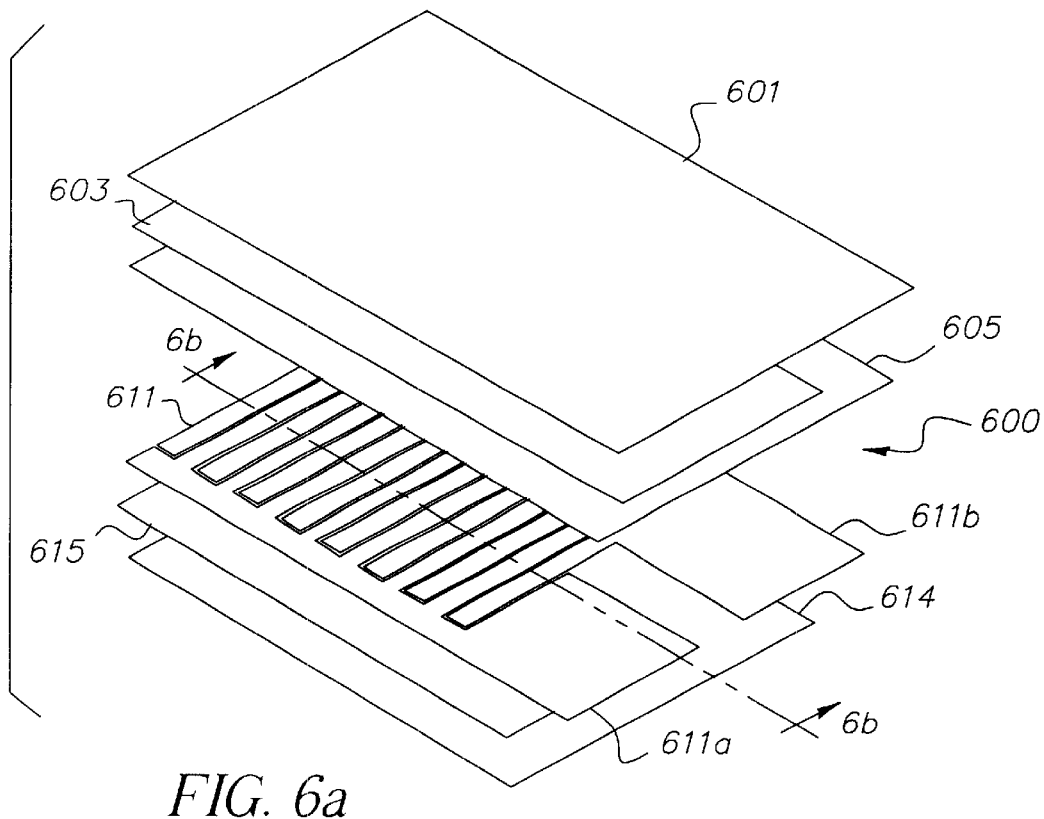
FIG. 6(a) shows another ambient condition sensor in accordance with the present invention.
Figure 6B:
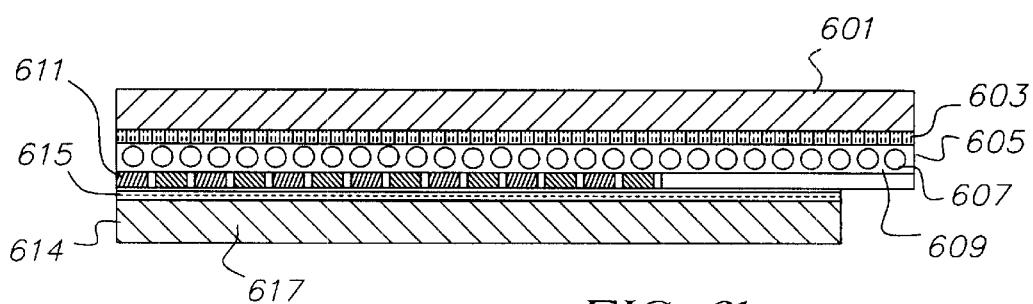
FIG. 6(b) is a cross sectional view of FIG. 6(a) taken along line 6b—6b.
Figure 6C:
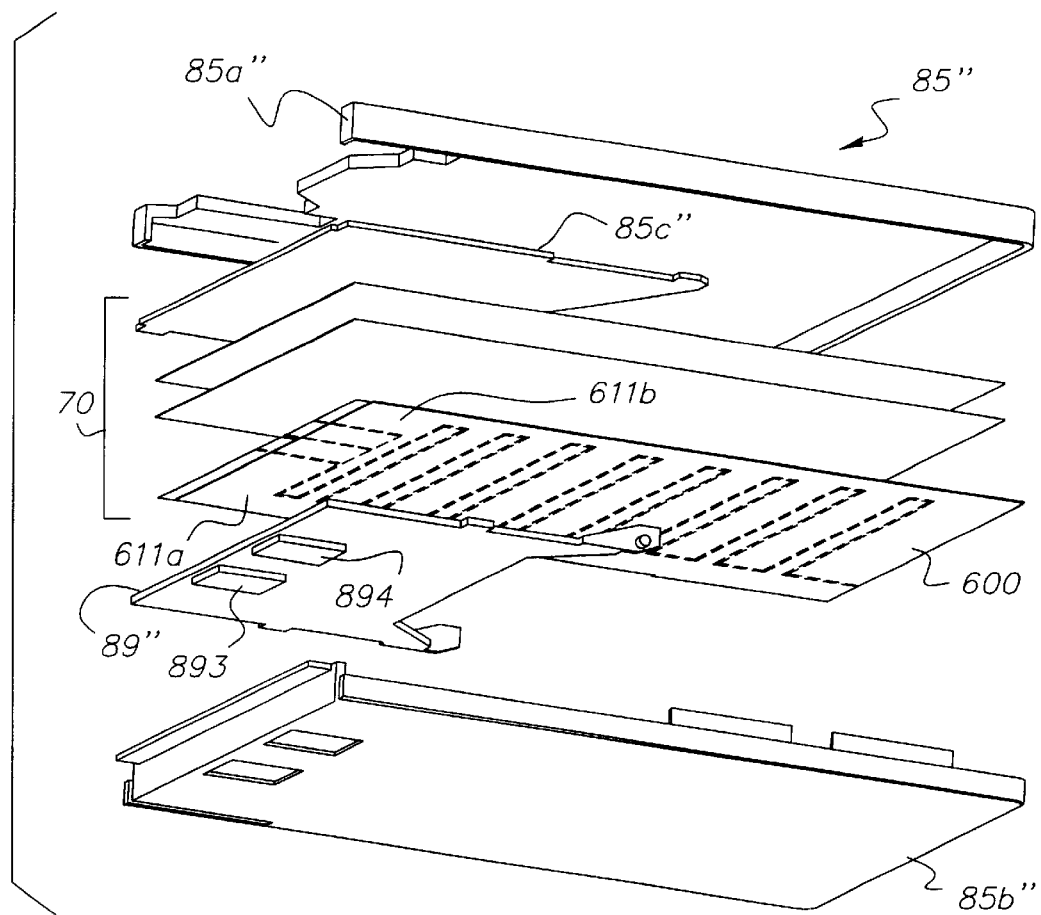
FIG. 6(c) shows another device for sensing ambient conditions in a photosensitive media cartridge in accordance with a further feature of the present invention.

FIGS. 6(a), 6(b) and 6(c) illustrate a further embodiment of an ambient condition sensor in accordance with the present invention. In the embodiment of FIGS. 6(a), 6(b), 6(c), the ambient condition sensor takes the form of the photosensitive media or material itself. Thus, the ambient condition sensor would comprise the same structure as the photosensitive media and also would be essentially pre-calibrated. FIG. 6(a) and 6(b) illustrates such a photosensitive media 600 sensor which acts as an ambient condition sensor. As shown in FIGS. 6(a) and 6(b), media 600 includes a first transparent support 601; a subbing layer 603; an image composition layer 605 which includes photo-hardenable microcapsules 607 and a developer material 609; a layer of adhesive 615; and a second support layer 614. Second support layer 614 may or may not contain an opacifying agent 617. For features of the photosensitive media reference is made to U.S. Pat. No. 5,783,353. The image composition layer 605 should be ionic in nature in order to be humidity responsive. To enhance the response of the image composition layer 605, an anti-static agent can be added during manufacturing. An example of an anti-static agent is a 50% solution of quaternary ammonium compound in isopropanol.

In a feature of the present invention as illustrated in FIGS. 6(a), 6(b), photosensitive media 600 further includes a layer 611 which is a conductive layer. In a preferred embodiment, conductive layer 611 is transparent, for example indium tin oxide (ITO), or matches the color of an opaque second support layer 614, and includes interdigited fingers having first and second electrical contacts 611a, 611b. As illustrated in FIG. 6(b), in a preferred embodiment of ambient condition sensor 600, second support layer 614 and adhesive layer 615 have a length which does not extend over the entire surface of electrical contacts 611a, 611b. On the other hand, the length of first transparent support 601 and subbing layer 603 matches the length of conductive layer 611 including electrical contacts 611a, 611b. This permits a portion of electrical contacts 611a, 611b to be exposed on one side. In this embodiment, humidity effects the electrical properties of the image composition layer 605 and the relative humidity can be obtained directly from the equivalent resistance or conductance of the sensor.

With the embodiment of FIGS. 6(a), 6(b), photosensitive media 600 can be positioned in a cartridge 85" as illustrated in FIG. 6(c). Cartridge 85" includes top and bottom sections 85a" and 85b". In one feature of the invention, only one photosensitive media of a stack of photosensitive media 70 in cartridge 85" would have the structure illustrated in FIG. 6(a) and would act as an ambient condition sensor. Photosensitive media 600 acting as an ambient condition sensor would be located at the bottom of the stack of photosensitive media 70, and would remain in cartridge 85" until all the other pieces of photosensitive media have been removed. Photosensitive media 600 acting as the ambient condition sensor would be calibrated to the media and would provide a true reflection of the ambient condition; such as humidity value, surrounding the media when the cartridge is inserted into an imaging device or apparatus. More specifically, electrical contacts 611a, 611b as shown in FIG. 6(b) would cooperate with conductive contact portions 893, 894 on spring plate 89" to provide an electrical signal to controller 30 located within the image-forming device to control development as previously described. Thus, an image-forming arrangement would be comprised of at least a cartridge which holds photosensitive media 600 that acts as an ambient condition sensor and image-forming device 15.

Figure 6D:
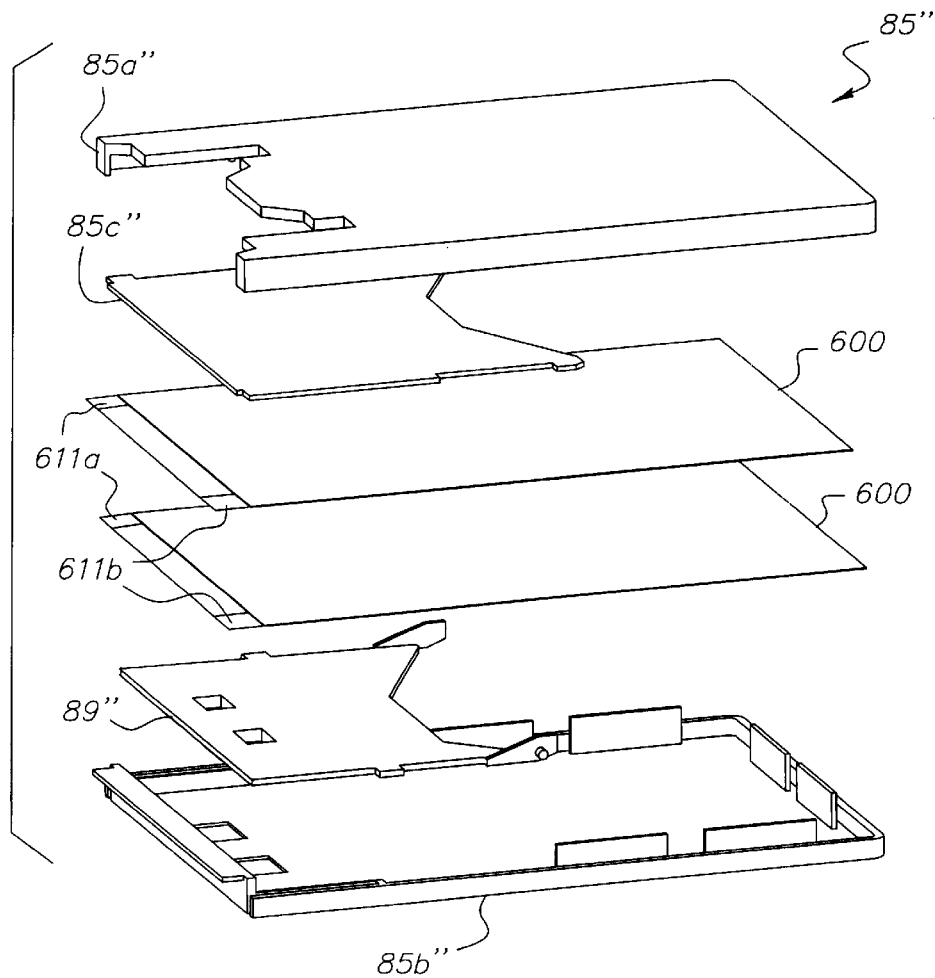
FIG. 6(d) shows another device for sensing ambient conditions in a photosensitive media cartridge in accordance with a further feature of the present invention.

As a further option, all of the media in the stack of photosensitive media could include a conductive layer, and thus each individual media would act as a separate ambient condition sensor as shown in FIG. 6(d).

Figure 7A:
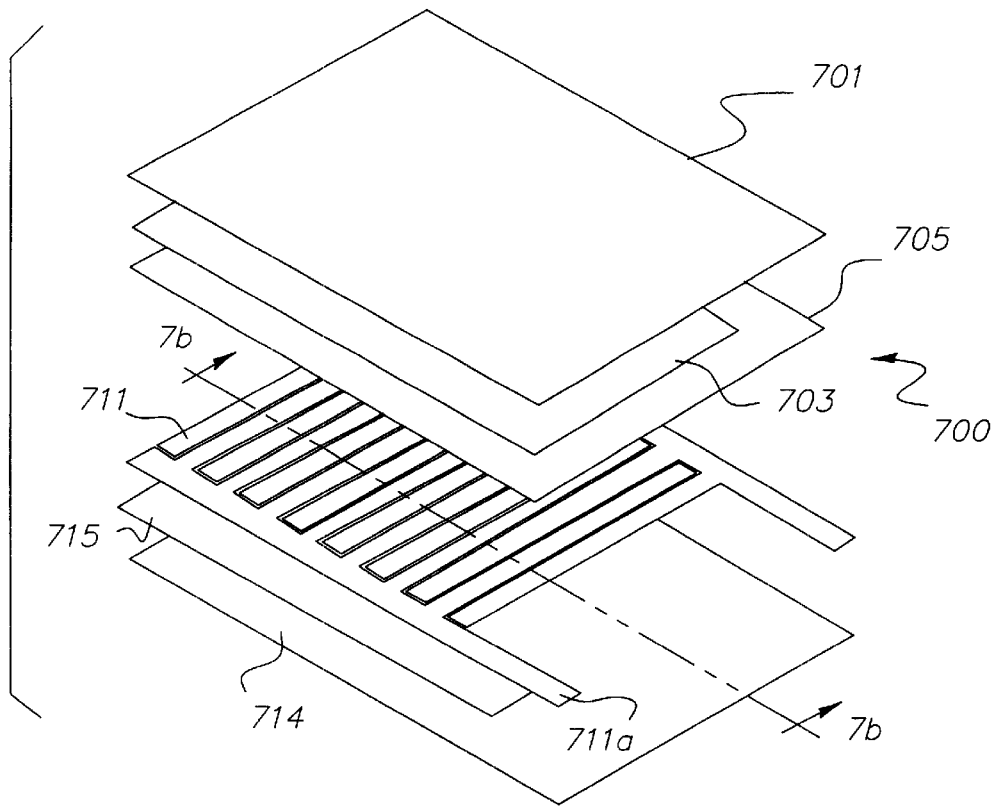
FIG. 7(a) shows yet another ambient condition sensor in accordance with the present invention.
Figure 7B:
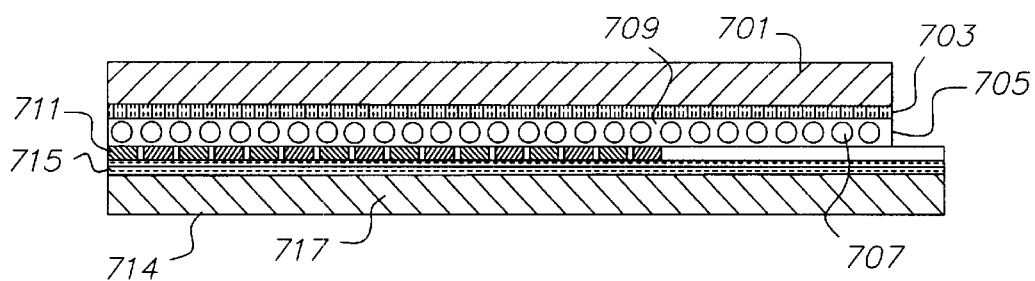
FIG. 7(b) is a cross sectional view of FIG. 7(a) taken along line 7b—7b.
Figure 7C:
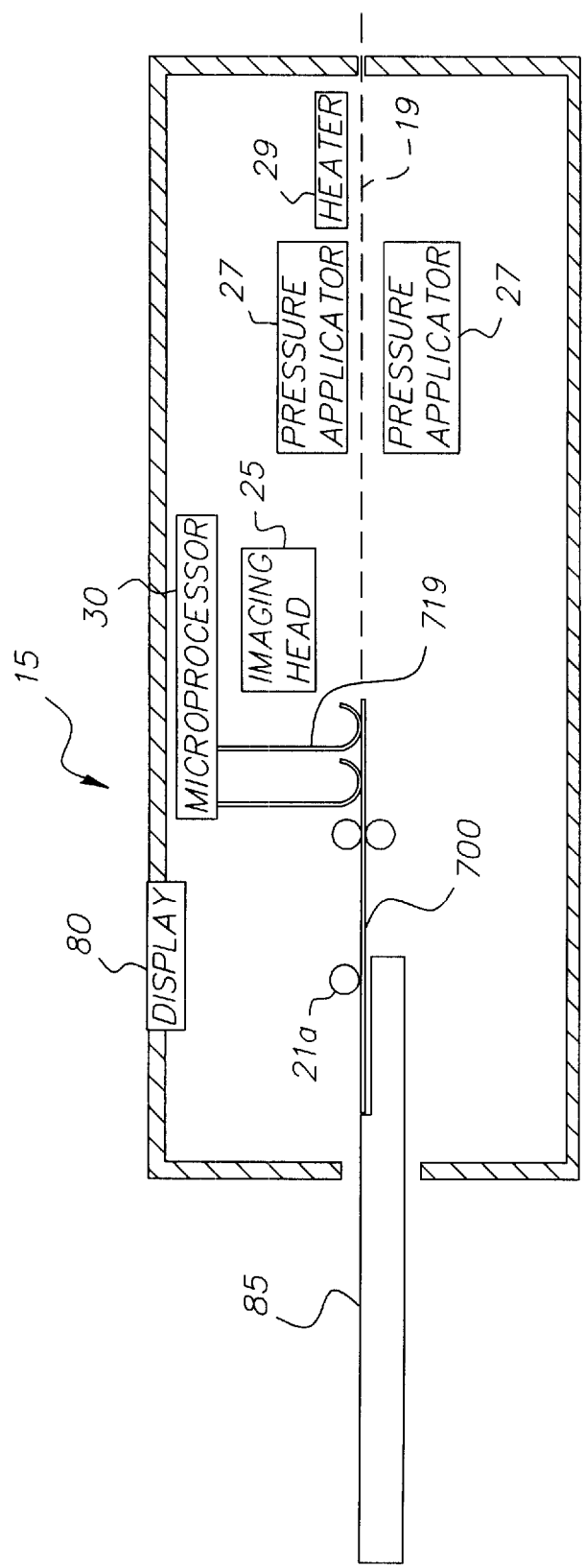
FIG. 7(c) schematically illustrates another example of an image-forming arrangement in accordance with the present invention.

FIGS. 7(a)–7(c) illustrates a further embodiment of an ambient condition sensor in accordance with the present invention. In the embodiment of FIGS. 7(a)–7(c), an ambient condition sensor takes the form of photosensitive media or material itself. Thus, the ambient condition sensor would comprise the same structure as the media and also would be essentially pre-calibrated. FIGS. 7(a) and 7(b) illustrate such a photosensitive media or ambient condition sensor 700. Ambient condition sensor 700 includes a first transparent support 701; a subbing layer 703; an image composition layer 705 which includes photo-hardenable microcapsules 707 and a developer material 709; a layer of adhesive 715; and a second support layer 714. Second support layer 714 may or may not contain an opacifying agent 717. For features of the photosensitive media reference is made U.S. Pat. No. 5,783,353.

In a feature of the present invention as illustrated in FIGS. 7(a) and 7(b), sensor 700 further includes layer 711 which is a conductive layer. In a preferred embodiment, conductive layer 711 is transparent or matches the color of an opaque second support layer 714. In the embodiment of FIGS. 7(a) and 7(b), conductive layer 711 includes electrical contacts 711a, 711b. As illustrated in FIG. 7(b), in a preferred embodiment of ambient condition sensor 700, first transparent support 701, subbing layer 703, and image composition layer 705 have a length which does not extend over the entire surface of electrical contacts 711a, 711b. On the other hand, the length of adhesive layer 715 and second support layer 714 matches the length of conductive layer 711 including electrical contacts 711a, 711b. This permits a portion of electrical contacts 711a, 711b to be exposed on one side which would be opposite to the exposed side of the electrical contacts in the embodiment of FIG. 6(b). In the embodiment of FIGS. 7(a)–7(b), humidity effects the electrical properties of the image composition layer 705 and the relative humidity can be obtained directly from the equivalent resistance or conductance of the ambient condition sensor.

With the arrangement of FIGS. 7(a), 7(b) with respect to the exposed side of contacts 711a, 711b, contact can be made as shown in FIG. 7(c). More specifically, as photosensitive media 700 which acts as an ambient condition sensor is withdrawn from cartridge 85 and is driven through the printing process along media path 19, conductive fingers 719 connected to controller 30 are positioned such that they make contact with electrical contacts 711a, 711b and transfer an electrical signal to controller 30. Like the embodiment noted above, it is recognized that photosensitive media 700 which acts as an ambient condition sensor is not limited for use in imaging apparatuses as illustrated in the present description. More specifically, the photosensitive media 700 which acts as an ambient condition sensor can be utilized in any imaging arrangement where it is desirable to control development based on ambient conditions surrounding media in a cartridge.

The invention has been described in detail with particular reference to certain preferred embodiments thereof, but it will be understood that variations and modifications can be effected within the spirit and scope of the invention.

What is claimed is:

1. An ambient condition sensor for a photosensitive material imaging arrangement, the ambient condition sensor comprising:
   a cover layer and a conductive layer, wherein a rate of response to ambient condition of said cover layer matches a rate of response to ambient conditions of a photosensitive material to be developed.

2. A sensor according to claim 1, wherein said cover layer is a humidity responsive layer and said conductive layer comprises conductive interdigited fingers and first and second electrical contacts.

3. A sensor according to claim 1, further comprising:
   an image composition layer, such that imaging properties of said ambient condition sensor matches imaging properties of the photosensitive material to developed.

4. A sensor according to claim 3, wherein said image composition layer comprise microcapsules which encapsulate imaging material.

5. A sensor according to claim 4, wherein said imaging material comprised coloring material.

6. A sensor according to claim 1, wherein said ambient conditions is reflective of humidity conditions around the photosensitive media.

7. An ambient condition sensor for sensing ambient conditions in a cartridge which holds photosensitive material, the ambient condition sensor comprising:
   a top layer, a humidity responsive layer, a conductive layer and a base support layer, wherein a rate of response to ambient conditions of at least one of said top layer, said humidity responsive layer, and said base support layer matches a rate of response to ambient conditions of photosensitive material in the cartridge.

8. A sensor according to claim 7, wherein said conductive layer comprises conductive interdigited fingers and first and second electrical contacts.

9. A sensor according to claim 7, wherein said ambient conditions is reflective of humidity conditions around the photosensitive material in the cartridge.

10. sensor according to claim 7, wherein a development of the photosensitive material is based on the sensed ambient conditions by said sensor.

11. A sensor according to claim 7, wherein said photosensitive material to be developed comprises microcapsules which encapsulate imaging material.

12. A sensor according to claim 11, wherein said imaging material comprises coloring material.

13. A method of producing an ambient condition sensor for photosensitive material to be developed, the method comprising:
   providing a cover layer on a conductive layer; and
   placing the conductive layer having the cover layer thereon in a cartridge which is adapted to hold photosensitive material to be developed therein, such that a rate of response to ambient conditions of at least the cover layer matches a rate of response to ambient conditions of the photosensitive material in the cartridge.

14. A method according to claim 13, wherein said cover layer is a humidity responsive layer and said conductive layer comprises conductive interdigited fingers and first and second electrical contacts.

15. A method of producing an ambient condition sensor according to claim 13, further comprising:
   adding an image composition layer to said conductive layer having said cover layer thereon, such that imaging properties of said ambient condition sensor matches imaging properties of the photosensitive material to be developed.

16. A method according to claim 15, wherein said image composition layer comprises microcapsules which encapsulate imaging material.

17. A method according to claim 16, wherein said imaging material comprises coloring material.

18. A method according to claim 13, wherein said ambient conditions is reflective of humidity conditions around the photosensitive media in the cartridge.

19. A method of controlling image development comprising:
   providing an ambient condition sensor in a cartridge which holds photosensitive media therein, said ambient condition sensor sensing ambient conditions around photosensitive media in the cartridge, said ambient condition sensor comprising at least a cover layer and a conductive layer, wherein a rate of response to ambient conditions of at least said cover layer matches a rate of response to ambient conditions of the photosensitive media in the media cartridge;
   inserting the cartridge to an insertion position in a printer which permits a passage of photosensitive media from the cartridge to the printer;
   sensing ambient conditions around the photosensitive media by way of the ambient conditions sensor; and
   controlling a development of images on the photosensitive media based on the sensed ambient conditions.

20. A method according to claim 19, wherein said cover layer is a humidity responsive layer and said conductive layer comprises conductive interdigited fingers and first and second electrical contacts.

21. A method according to claim 19, further comprising:
adding an image composition layer to said conductive layer having said cover layer thereon, such that imaging properties of said ambient condition sensor matches imaging properties of the photosensitive media in the cartridge.

22. A method according to claim 21, wherein said image composition layer comprises microcapsules which encapsulate imaging material.

23. A method according to claim 22, wherein said imaging material comprises coloring material.

24. A method according to claim 19, wherein said ambient conditions is reflective of humidity conditions around the photosensitive media in the cartridge.

* * * * *